(12) United States Patent
Asmussen et al.

(10) Patent No.: US 11,612,571 B2
(45) Date of Patent: Mar. 28, 2023

(54) TRANSDERMAL THERAPEUTIC SYSTEM FOR ADMINISTERING WATER-SOLUBLE PEPTIDES AND POLYPEPTIDES

(75) Inventors: Bodo Asmussen, Bendorf (DE); Michael Horstmann, Neuweid (DE); Christoph Schmitz, Rheinbrohl (DE); Mohammad Sameti, Bonn (DE); Yves-Thorsten Przybylla, Nickenich (DE); Rolf Pracht, Höhr-Grenzhausen (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 256 days.

(21) Appl. No.: 12/525,888

(22) PCT Filed: Jan. 19, 2008

(86) PCT No.: PCT/EP2008/000392
§ 371 (c)(1),
(2), (4) Date: Aug. 5, 2009

(87) PCT Pub. No.: WO2008/095597
PCT Pub. Date: Aug. 14, 2008

(65) Prior Publication Data
US 2010/0028412 A1 Feb. 4, 2010

(30) Foreign Application Priority Data
Feb. 8, 2007 (DE) .................. 10 2007 006 244.5

(51) Int. Cl.
*A61K 9/70* (2006.01)
*A61K 31/135* (2006.01)
(52) U.S. Cl.
CPC .......... *A61K 9/7084* (2013.01); *A61K 31/135* (2013.01)

(58) Field of Classification Search
None
See application file for complete search history.

(56) References Cited

U.S. PATENT DOCUMENTS

| 4,597,961 | A | * | 7/1986 | Etscorn | A61K 9/7084 424/448 |
| 4,719,239 | A | * | 1/1988 | Muller | A61K 9/0014 514/785 |

(Continued)

FOREIGN PATENT DOCUMENTS

| CA | 2341643 | 3/2000 |
| DE | 4223004 | 7/1992 |

(Continued)

OTHER PUBLICATIONS

Online dictionary, definition of transcutaneous.*

(Continued)

*Primary Examiner* — Isis A Ghali
(74) *Attorney, Agent, or Firm* — ProPat, LLC; Cathy Moore

(57) ABSTRACT

The invention relates to a transdermal therapeutic system for the controlled release of water-soluble pharmaceutical active ingredients from an aqueous phase, comprising an occlusive back layer, a central device facing the skin for releasing the agent, an adhesive layer concentrically surrounding the dispensing device and a removable protective film. Said device is made from a stationary solid phase and a liquid phase containing the active ingredient in aqueous solution, the solid phase being formed from a solid with a fleecy or spongy structure.

15 Claims, 2 Drawing Sheets

(56) References Cited

U.S. PATENT DOCUMENTS

| | | | | |
|---|---|---|---|---|
| 4,784,857 | A | * | 11/1988 | Berry .................. A61K 9/7084 424/443 |
| 4,994,049 | A | * | 2/1991 | Latzke et al. ................. 604/307 |
| 5,100,672 | A | | 3/1992 | Gueret et al. |
| 5,244,677 | A | * | 9/1993 | Kreckel et al. ............... 424/448 |
| 5,462,743 | A | * | 10/1995 | Turner ................ A61F 13/0226 424/448 |
| 5,686,112 | A | | 11/1997 | Liedtke |
| 5,707,641 | A | * | 1/1998 | Gertner et al. ............... 424/422 |
| 5,807,570 | A | * | 9/1998 | Chen .................. A61K 31/4015 424/449 |
| 6,328,992 | B1 | * | 12/2001 | Brooke et al. ............... 424/449 |
| 2001/0038862 | A1 | * | 11/2001 | Luo ..................... A61K 9/7023 424/688 |
| 2003/0133970 | A1 | | 7/2003 | Bracht et al. |
| 2003/0147943 | A1 | | 8/2003 | Luo et al. |
| 2004/0247657 | A1 | | 12/2004 | Susilo |
| 2005/0074487 | A1 | | 4/2005 | Hsu et al. |
| 2005/0244484 | A1 | | 11/2005 | Hsu et al. |
| 2006/0093659 | A1 | | 5/2006 | Luo et al. |
| 2008/0175891 | A1 | * | 7/2008 | Stover ................. C07H 19/052 424/449 |

FOREIGN PATENT DOCUMENTS

| | | |
|---|---|---|
| DE | 19849823 | 5/2000 |
| DE | 10027258 | 10/2001 |
| EP | 0412869 | 4/1994 |
| IN | 187032 | 12/2001 |
| JP | 01-224312 | 9/1989 |
| JP | 07-277961 | 10/1995 |
| JP | 8-509200 | 10/1996 |
| WO | WO 90/07328 | 7/1990 |
| WO | WO 2004/060447 | 7/2004 |
| WO | WO 2005/037157 | 4/2005 |

OTHER PUBLICATIONS

Webster's II dictionary, definition of transcutaneous.*
Online dictionary, definition of transdermal.*
Treffel et al., Effect of Occlusion on vitro Percutaneous Absorption of Two Compounds with Different Physicochemical Properties, Skin Pharmacol, 1992, 5, 108-113.
Bucks et al., Bioavailability of Topically Administered Steroids: A "Mass Balance" Technique, J.Investigative Dermatology, Jul. 1988, 91, 29-33.
Zelis et al., "Calcium Blocking Drugs for Angina Pectoris," Ann. Rev. Med. (1982) vol. 33, pp. 475-476.

* cited by examiner

TRANSDERMAL THERAPEUTIC SYSTEM FOR ADMINISTERING WATER-SOLUBLE PEPTIDES AND POLYPEPTIDES

Transdermal therapeutic systems have been established on the market for numerous active substances for a number of years. Administration forms of this kind allow the cutting of skin-permeable active pharmaceutical substances through the healthy human skin for the purpose of obtaining systemic therapeutic effects. In general, pharmaceutical active-substance patches of this kind are based on what are known as matrix patches or reservoir/membrane patches which comprise the active substance embedded in dissolved or crystalline form in a predominantly lipophilic polymer. Numerous technologies are also based on the addition of predominantly lipid-soluble excipients which in some cases are intended to produce enhanced bond strength or diffusiveness of the active substance and on the other hand are also aimed at boosting the absorption effect of the skin itself.

The delivery of predominantly hydrophilic active substances to the human skin that are of limited solubility in lipophilic media has to date been less of a subject of intense research. It is true that there are hydrogel systems known whose adhesive matrix facing the skin is composed predominantly of water and thus allows the use of highly water-soluble active substances. A disadvantage of such systems, however, is that pharmaceutical active substances, especially those of high molecular mass, are greatly hindered in their diffusion before they reach the skin, as a result of the polymeric gel framework that is present.

U.S. Pat. No. 5,707,641 describes a pharmaceutical formulation, composed of an aqueous emulsion or dispersion, intended more particularly for transdermal administration, which further to the aqueous phase comprises as active substance a pharmaceutically active protein or polypeptide, an emulsifier, and an oily phase. The patent specification further discloses a matrix for the transdermal administration of the stated formulation, composed of a porous, absorbent, and monolaminar solid material that comprises said formulation in absorbed form. The matrix may further be provided with a flexible, breathable (i.e., nonocclusive) backing layer.

EP 0 412 869 B1 proposes a composite film for local treatment of the skin surface, comprising an occlusive layer and a reservoir layer. The latter is formed from a matrix consisting of a silicone polymer and, within internal inclusions, comprises an aqueous gel layer with an active pharmaceutical substance. For the purpose of reinforcement, the reservoir layer may include an inlay of perforated fiber nonwoven, but this inlay is not in contact with the active substance gel. From the description and the claims it is clear that this composite film is suitable only for local treatment of the skin, since there are no measures indicated that ensure the controlled release of the active substance that is necessary for systemically transdermal administration.

The last-mentioned defect is also present in proposals for the administration of aqueous active substance formulations, as per Indian patent specification IN 187032 and also DE 42 23 004 A1, which describe the administration of undosed aqueous formulations to the skin. Neither of these publications discloses a solution for a really precise application to the human skin or for unhindered diffusion of water-soluble active substances. The prior art, furthermore, does not specify any solution for the problem of protection from evaporation. Complex pharmaceutical preparations which comprise volatile ingredients, especially water, suffer on the skin from unanticipable changes in the formulation as a result of evaporation of the volatile fraction. The problem is therefore not removed by simple application to the skin or possibly the application of pure foils, since the liquid active substance formulations spread uncontrolledly on the skin and so increase the area of action, and since, moreover, no fixing of the active substance on the skin is ensured.

For some considerable time it was considered to be a fact set in stone that the presence of an impermeable (occlusive) backing layer in transdermal therapeutic systems generally increases the skin permeation of active substances (Ann. Red. Med., Vol. 33, 18 (1982); p. 475, 476, U.S. Pat. No. 4,597,961 (1986), column 2, lines 61-65). More recent publications, however, have shown that under occlusive conditions, penetration or permeation of the human skin is increased only by lipophilic active substances, whereas that by hydrophilic and low-lipophilicity active substances remains unchanged (Bucks, D. A. et al, J. Invest Dermatol 1988 July; 91(1): 29-33; Treffel P.; Skin Pharmacol. 1992, 5(2), 108-113).

Surprisingly it has now been found that the transdermal therapeutic system of the invention, comprising a continuous, concentrically disposed, water-insoluble adhesive-layer margin, an occlusive backing layer impermeable for the active substance, a device facing the skin and intended for the delivery of a hydrophilic active substance from an aqueous phase, and a detachable protective foil permits the controlled release of the active substance from the delivery device and permits increased permeation through the skin.

The transdermal therapeutic system of the invention can be described in detail as follows:

The central device for delivering the active substance is composed of two phases, the stationary solid phase being formed from a solid, which may be flexible and which has a fibrous or open-pore fleece- or spongelike structure, and the liquid phase being composed of an aqueous solution, emulsion or suspension that comprises the pharmaceutically active substance.

The two-phase delivery device is concentrically surrounded by an adhesive-layer margin consisting of a customary adhesive polymer. In one preferred embodiment of the invention this margin is reinforced in thickness by a layer of nonadhesive polymers, which may also be present in the form of closed-pore foams. Through the thickness of this layer, which is in a range of 200-5000 µm, preferably of 500-2000, it is also possible to regulate the space for the central delivery device.

The delivery device may be circular or may represent a square or rectangle whose angles may be rounded or beveled (FIG. 1). In the case of a circular delivery device, the adhesive-layer margin has an annular form.

The present invention is elucidated further by the figures, FIG. 1 and FIG. 2.

Figure 1:
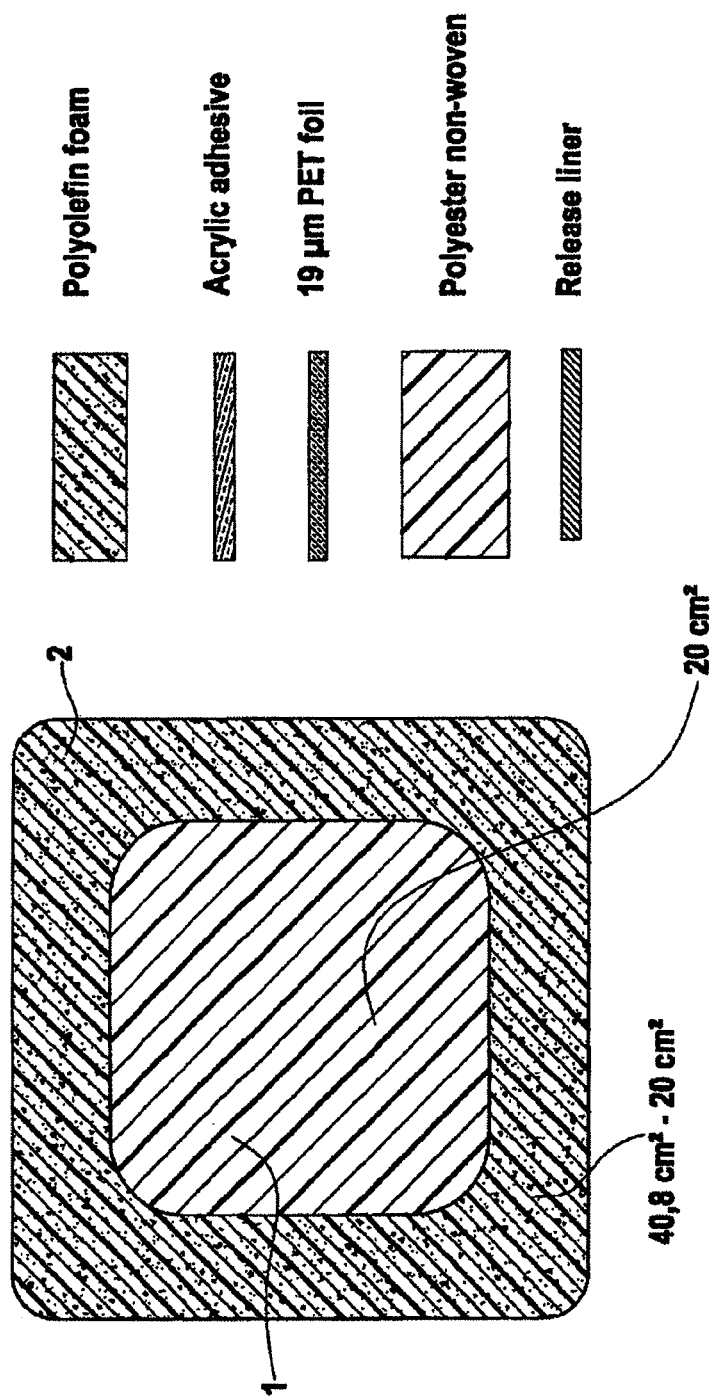
FIG. 1 shows the plan view of a transdermal therapeutic system of the invention.
Figure 2:
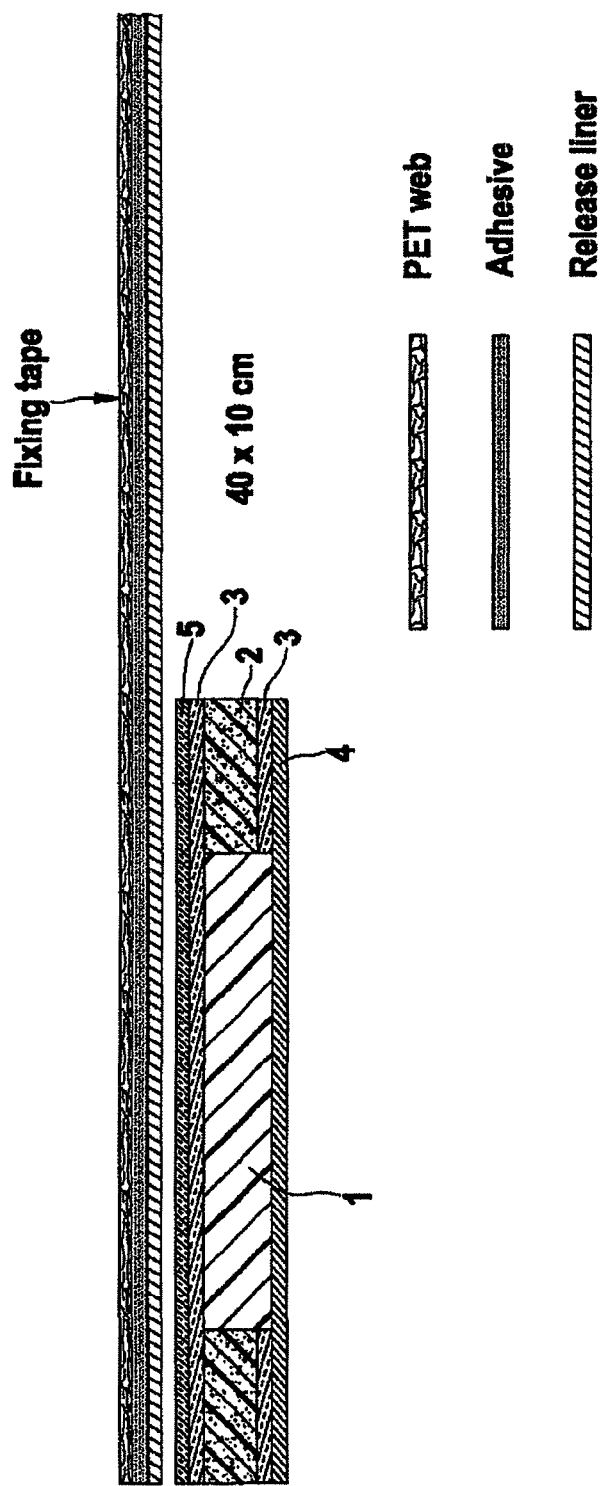
FIG. 2 shows a cross section through the system of the invention.

1 represents the central delivery device, 2 a layer of at least one nonadhesive polymer, 3 an adhesive layer, 4 a release liner, and 5 an occlusive backing layer.

The stationary phase of the central delivery device is a solid phase which may be rigid or flexible and which has a fibrous, open-pore, fleece- or spongelike structure. Materials contemplated for this solid phase include substances from the group of synthetic or natural fiber materials, e.g., cellulose, viscose, polyester fibers, polyurethane fibers, silicone fibers, etc. Preference is given to materials referred to as nonwovens.

As the liquid phase of the central delivery device, use is made of aqueous solutions of active pharmaceutical substances which are hydrophilic—that is, readily water-soluble; this aqueous solution may also be part of an emulsion or suspension.

In addition to the excipients that are needed to form an emulsion or suspension, the liquid phase may comprise further excipients which permit, for example, the formation of liposomes.

Hydrophilic active substances in the context of the invention are meant those which have a higher solubility in water than in organic media. This group includes numerous drugs whose transdermal use was hitherto possible either not at all or only to a limited degree. They include, for example, adrenalin, heparin, methoclopramide hydrochloride, salbutamol hydrochloride, and also peptides or polypeptides, such as vasopressin, insulin, somatotropin or calcitonin, for example.

For the occlusive backing layer, olefinic foils are contemplated, such as, for example, those of polyethylene, polypropylenes or polyurethanes, but preferably a polyethylene terephthalate foil. The adhesive-layer margin may be composed of polymers of the polyisoprene group, polyisobutylene group or polyacrylic ester group or else of polysiloxane copolymers.

The layer of nonadhesive polymer which serves to reinforce the adhesive-layer margin is composed of polyolefins, preferably of a foam of at least one of these materials.

The following examples of semisolid or liquid active substance formulations are intended to elucidate the invention without restricting it.

EXAMPLE 1

A Semisolid Formulation

| | |
|---|---|
| Aqua purificata | 10 g |
| Sodium benzoate | 0.03 g |
| Bile salts | 0.8 g |
| Cholesterol | 0.7 g |
| Polyoxyethylene | 0.8 g |
| Peptide | 0.1 g |
| SDS | 0.5 g |
| Glycerol | 2.0 g |

EXAMPLE 2

A Liquid Formulation

| | |
|---|---|
| Aqua purificata | 10 g |
| Parahydroxybenzoic acid (PHB) | 0.03 g |
| Peptide | 0.1 g |
| Marcrogol | 0.8 g |
| Sorbitan monostearate | 0.8 g |
| Triglyceride medium chain | 0.5 g |
| Glycerol | 1.0 g |

The invention claimed is:

1. A transdermal therapeutic system for controlled delivery of a water-soluble, active pharmaceutical substance from an aqueous phase, comprising:
an occlusive backing layer having first and second surfaces which is impermeable for the active pharmaceutical substance and comprises an olefinic foil or a polyethylene terephthalate foil;
a first adhesive layer disposed on the first surface of the backing layer
a central device facing the skin for delivery of the active pharmaceutical substance, said central device comprising:
a stationary solid phase; and a liquid phase;
said liquid phase is either an aqueous solution or suspension and not either a semisolid or an emulsion, said liquid phase comprising the active substance;
the solid phase has a fibrous, open-pore structure, and is made from at least one material selected from polyester, polyurethane, and silicone;
the fibrous, open-pore structure has open space in which the liquid phase is arranged;
a second adhesive layer defining the outer margin of the central delivery device by surrounding and concentrically contacting the central delivery device;
a redetachable protective foil is disposed on said second adhesive layer and said central delivery device;
wherein the water-soluble active pharmaceutical substance is a peptide or polypeptide and
the surface area of the central delivery device is defined by layers and foil consisting of the first adhesive layer, the protective foil, the second adhesive layer and a non-adhesive polymer layer of closed pore foam for reinforcement disposed between the second adhesive layer and the first adhesive layer.

2. The transdermal therapeutic system of claim 1; wherein the solid phase of the central delivery device is rigid.

3. The transdermal therapeutic system of claim 1; wherein the solid phase further comprises at least one synthetic and/or natural fiber material.

4. The transdermal therapeutic system of claim 1; wherein the liquid phase of the central delivery device consists essentially of an aqueous solution of the active pharmaceutical substance.

5. The transdermal therapeutic system of claim 1; wherein the occlusive backing layer is impermeable for the active pharmaceutical sub stance.

6. The transdermal therapeutic system of claim 1; wherein the adhesive layer concentrically surrounding the central delivery device comprises an adhesive polymer.

7. The transdermal therapeutic system of claim 6; wherein the adhesive layer is reinforced by at least one layer of nonadhesive polymers, where the nonadhesive polymer increases the thickness of the adhesive layer.

8. The transdermal therapeutic system of claim 1; wherein the solid phase of the central delivery device is flexible.

9. The transdermal therapeutic system of claim 7, wherein the nonadhesive polymer is a foam.

10. A transdermal therapeutic system for controlled delivery of a water-soluble, active pharmaceutical substance from an aqueous phase, comprising:
an occlusive backing layer which is impermeable for the active pharmaceutical substance and comprises an olefinic foil or a polyethylene terephthalate foil onto which a first adhesive layer is disposed;
a central device facing the skin and intended for delivery of the active pharmaceutical substance, said central device comprising:
a stationary solid phase; and a liquid phase;
wherein said liquid phase comprises the active substance in an aqueous solution, suspension or emulsion;

wherein the solid phase has a fibrous, open-pore structure, and is made from at least one material selected from polyester, polyurethane, and silicone;

wherein the fibrous, open-pore structure has open space in which the liquid phase is arranged;

a second adhesive layer defining the outer margin of the central delivery device by concentrically surrounding and contacting the central delivery device;

a redetachable protective foil; and the first adhesive layer is disposed between the occlusive backing layer and the central delivery device;

wherein the water-soluble active pharmaceutical substance is a peptide or polypeptide other than insulin, and the second adhesive layer is a continuous layer disposed on both the first adhesive layer and the protective foil, and the surface area of the central delivery device is defined by layers and foil consisting of the first adhesive layer, the protective foil and the second adhesive layer and a non-adhesive polymer layer of closed pore foam for reinforcement disposed between the second adhesive layer and the first adhesive layer.

11. The transdermal therapeutic system of claim 10, wherein said second adhesive layer is formed from acrylic adhesive and the liquid phase is an emulsion.

12. The transdermal therapeutic system of claim 1, wherein said transdermal therapeutic system comprises a single central delivery device.

13. The transdermal therapeutic system of claim 1, wherein the central device has a thickness and the second adhesive layer and the non-adhesive polymer layer are disposed on the full thickness of the central device.

14. The transdermal therapeutic system of claim 1, wherein the fibrous, open-pore structure is a nonwoven.

15. The transdermal therapeutic system of claim 1, wherein the fibrous, open-pore structure is made from material consisting of at least one material selected from polyester and silicone.

* * * * *